United States Patent [19]

Hudziak et al.

[11] 4,440,173

[45] Apr. 3, 1984

[54] PROGRAMMABLE BODY STIMULATION SYSTEM

[75] Inventors: Lawrence C. Hudziak, White Bear Lake; Jerome T. Hartlaub, New Brighton, both of Minn.

[73] Assignee: Medtronic, Minneapolis, Minn.

[21] Appl. No.: 280,222

[22] Filed: Jul. 6, 1981

Related U.S. Application Data

[63] Continuation of Ser. No. 92,354, Nov. 8, 1979, abandoned.

[51] Int. Cl.³ .............................................. A61N 1/36
[52] U.S. Cl. .............................................. 128/419 PG
[58] Field of Search ................................ 128/419 PG

[56] References Cited

U.S. PATENT DOCUMENTS 3,717,153  2/1973  Bowers ...................... 128/419 PG
4,066,086  1/1978  Alferness et al. ............ 128/419 PG

*Primary Examiner*—William E. Kamm
*Attorney, Agent, or Firm*—Schroeder, Siegfried, Vidas & Arrett

[57] ABSTRACT

A body stimulation system including external components for generating and transmitting programming signals and implantable components including a signal generator with at least one alterable operating characteristic, a stimulation signal delivering system and circuit responsive to receive programming signals for establishing the operating characteristic in predetermined correspondence therewith. The stimulation signal delivering system is connected to the operating characteristic establishing circuitry for receiving the programming signals. In a preferred embodiment, the external components are prevented from transmitting programming signals during a stimulation signal and, more preferably, for a predetermined period following a stimulation signal. The predetermined period may be established such that the external system is activated during the refractory period of the tissue being stimulated. The external system may provide a programming signal and a second signal having characteristics discriminable from the characteristics of the programming signal such that the operating characteristic establishing circuitry is responsive to a received programming signal only during the occurrence of the second signal. The pulse generator of the implantable unit may also respond to the second signal to operate at a fixed rate during the second signal.

11 Claims, 1 Drawing Figure

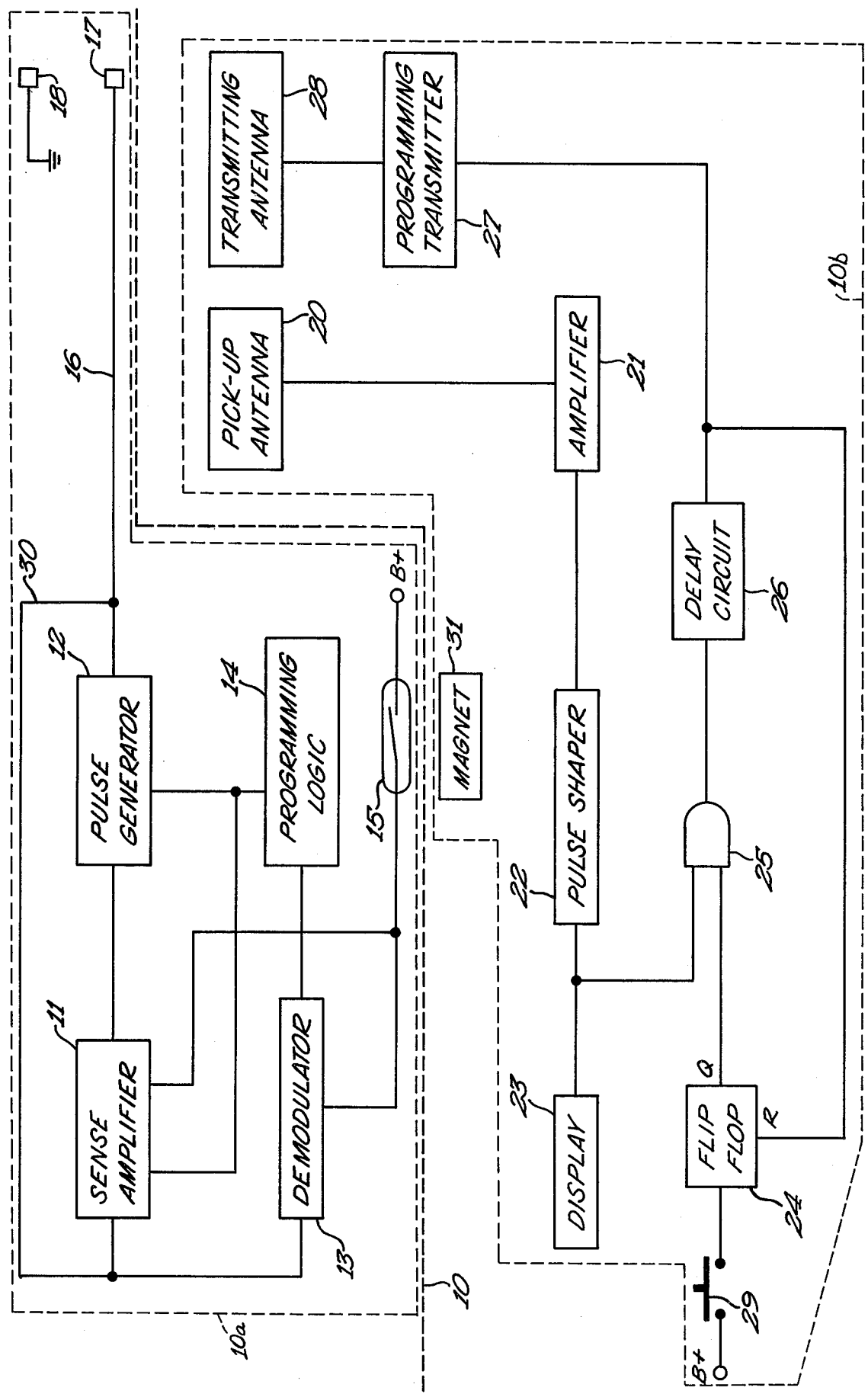

PROGRAMMABLE BODY STIMULATION SYSTEM

This is a continuation of parent application Ser. No. 92,354, filed on Nov. 8, 1979 in the name of Lawrence Hudziak et al., now abandoned.

BACKGROUND OF PRIOR ART

Programmable body implanatable stimulators are known to the prior art. Their programming has been variously accomplished as through the use of a magnetic field operating on an implanted reed switch, the use of radio frequency energy transmitted to an antenna within the implanted unit and through the use of a Keith needle. A magnetic field alone has the obvious disadvantage of being easily duplicated by extraneous fields to result in an undesired programming. A Keith needle requires a penetration of the body. The radio frequency energy approach, as implemented in the prior art, has also had its drawbacks.

One system which combines a magnetic field with a radio frequency signal for the programming of a body implantable stimulator is disclosed in U. S. Pat. No. 4,066,086 issued Jan. 3, 1978, to Clifton A. Alferness et al. for PROGRAMMABLE BODY STIMULATOR, which is hereby incorporated by reference. Another programmable unit is disclosed in application Ser. No. 957,813 now U.S. Pat. No. 4,275,737 filed Nov. 6, 1978, in the name of Jerome T. Hartlaub et al. for DEMAND CARDIAC PACEMAKER HAVING REDUCED POLARITY DISPARITY, which is commonly owned with the present invention and which is also incorporated herein by reference.

Many prior art implantable stimulators have been formed by molding the components, including mechanical and electrical connections for the lead, in a matrix of encapsulating material which supports the components and shields them from the body environment. Typically, the encapsulating material is an epoxy. However, it is generally recognized that an enclosed and hermetically sealed unit is more reliable as a result of the known and controlled environment provided by the hermetic seal. For this reason, many recent signal generator designs include a rigid enclosure formed of a plurality of preformed members which are typically welded together to complete the enclosure. In the context of a programmable unit, however, absorption, reflection and attenuation of radio frequency energy by the metal enclosure complicates the programming operation. These programming problems are further compounded by power transmission limits established by the FCC and the trend towards smaller and smaller units.

BRIEF SUMMARY OF THE INVENTION

The present invention is directed to a body stimulation system of the type having an external unit for generating and transmitting radio frequency programming signals and an implantable unit including a stimulation signal generator with at least one alterable operating characteristic, an output system for delivering a stimulation signal to the desired body site and circuitry responsive to received programming signals for establishing the operating characteristic in predetermined correspondence therewith. The output delivering system is connected to the operating characteristic establishing circuitry and receives the programming signals and delivers the same to the operating characteristic establishing circuitry. In a preferred embodiment, the output delivering system includes a stimulation delivering lead, the lead receiving and delivering the programming signals to the operating characteristic establishing circuitry. Thus, antenna coils of prior art programmable devices are eliminated, without elimination of their function. In addition, in the event that the stimulation signal generator is hermetically sealed in a housing, as described above, that housing does not interfere with the reception of the programming signals by the implantable device. To assure the integrity of the programming signal, the external device is prevented from transmitting a programming signal during a stimulation signal. Preferably, such transmission is prevented for a predetermined time following a stimulation signal. The predetermined period may be such that the external device is activated to transmit a programming signal only during the refractory period of the tissue being stimulated. In order to limit programming of the implantable device by extraneous signals, the operating characteristic establishing circuitry may be rendered responsive to receive programming signals only during the occurrence of second externally generated signals having characteristics discriminable from the characteristics of the programming signals. In a preferred embodiment, the programming signals comprise radio frequency signals and the second signals comprise magnetic signals. In the event that the stimulation signal generator is a pulse generator, it may be caused to operate at a fixed rate during the occurrence of the second externally generated signals.

BRIEF DESCRIPTION OF THE DRAWINGS

The single FIGURE illustrates in diagrammatic form the implantable and external units forming the system of the present invention.

DETAILED DESCRIPTION OF INVENTION

The FIGURE illustrates, in diagrammatic form, a preferred embodiment of the present invention including internal and external units. A dotted line 10, which may represent the skin, separates the external unit (positioned beneath the dotted line 10) from the implantable unit (positioned above the dotted line 10). Both the implantable and external units may be housed, as desired, with the implantable unit being housed in a manner which will protect its components from the body environment, in known manner. The dotted lines 10a and 10b, respectively, represent such housings.

The implantable unit includes a sense amplifier 11, a pulse generator 12, a demodulator 13, programming logic 14, a reed switch 15 and a stimulation energy delivery system including a lead 16, an active electrode 17 carried by the lead 16, and an indifferent electrode 18, together with their interconnections which will be described more fully below. The external unit includes a pick-up antenna 20, an amplifier 21, a pulse shaper 22, a display 23, a flip-flop 24, and AND gate 25, a delay circuit 26, a programming transmitter 27, a transmitting antenna 28 and a normally open switch designated generally at 29, together with their interconnections which will be described more fully below. Generally speaking, the external unit transmits a programming signal via transmitting antenna 28, the transmitting signal being established by programming transmitter 27. The programming signal is received by lead 16 and demodulated by demodulator 13 to result in a reprogramming of sense amplifier 11 and pulse generator 12 by programming logic 14. Pick-up antenna 20 senses stimulation signals applied to the lead 16, those signals being amplified and shaped to result in a display at display 23. Display 23 allows an external monitoring of the stimulation signals applied to lead 16 to establish that a reprogramming has been accomplished. Additionally, the signals picked up at pick-up antenna 20 are processed by AND gate 25 and delay circuit 26, together with a manual input entered at switch 29 which is operative on flip-flop 24, to establish a desired relative timing between a stimulation energy signal and a programming signal.

Sense amplifier 11 and pulse generator 12 are connected to function as a demand cardiac pacemaker. That is, signals sensed between electrdoe pair 17/18 resulting from natural heart activity will be applied to the input of sense amplifier 11 via line 30 to result in a reset signal being applied to pulse generator 12 to restart its timing cycle. In the event that natural heart activity is not detected between electrode pair 17/18 during the timing cycle of pulse generator 12, pulse generator 12 will deliver a pluse of stimulation energy to the lead 16 to be applied between the electrode pair 17/18. The operation of sense amplifier 11 and pulse generator 12, together with any desired noise rejection circuitry, output driving circuitry, etc., is known to the prior art. It is also known to employ a received programming signal, demodulated by demodulator 13, to result in a reprogramming of pulse generator 12 and sense amplifier 11 via programming logic 14. Such operating characteristics as pulse rate, pulse width, and pulse amplitude together with mode of operation, hysteresis, etc., have been programmed in this manner. It is further known to disable the sense amplifier 11 during the programming signal, as by closure of the reed switch 15 in the presence of a magnetic field, to cause the pulse generator 12 to operate in an asynchronous or fixed rate. The demodulator 13 may be enabled only during closure of the reed switch 15 so as to limit the potential for a false programming via extraneous noise. Each of these features are illustrated by the interconnections shown with reference to the implantable unit in the Figure. However, the prior art receiving antenna, which formed a part of the implantable unit and was typically encapsulated or housed therewith, is not illustrated in the Figure. Instead, the lead 16, which may be any of a variety of prior art leads, is connected directly to demodulator 13 to serve as the receiving element for the radio frequency programming signals. Thus, the programming capability is maintained while eliminating a component previously necessary to accomplish that end. In addition, in the event that the stimulation signal generating components and the reprogramming components are enclosed in a hermetically sealed housing, the use of lead 16 as the receiving element, being external to the metallic housing, eliminates the prior art difficulties of metal absorption, reflection and attenuation of radio frequency energy resulting from the prior art placement of the receiving antenna within the metallic housing.

The external unit includes a magnet 31 which, when placed in sufficiently close proximity to the implanted reed switch 15, results in a closing of the reed switch 15 and an enabling of demodulator 13 and disabling of sense amplifier 11, as discussed above. In this condition, the stimulation signal generating components of the implanted unit will operate in a fixed rate or an asynchronous mode while the demodulator will accept a programming signal received at lead 16.

A stimulation signal applied to lead 16 will result in a radio frequency signal which may be detected by pick-up antenna 20. The resulting signal may be amplified at amplifier 21 and shaped by pulse shaper 22 which may include a Schmitt trigger, in known manner, to be displayed at display 23. Display 23 may be any conventional display allowing the monitoring of such stimulation signal parameters as pulse rate, pulse width and pulse amplitude, for example. Thus, elements 20-23 and 31 of the external unit allow an external, non-invasive monitoring of the present programmed state of the pulse generator 12. Of course, if the programmed state includes operation in the demand mode, magnet 31 may be removed allowing reed switch 15 to open to determine how often stimulation signals are delivered as well as the parameters of those signals.

The output from pulse shaper 22 is applied as one input to an AND gate 25. The Q terminal of flip-flop 24 is connected to the other input of AND gate 25 while the output of AND gate 25 is connected to a delay circuit 26. The output of delay circuit 26 is connected to the reset terminal of flip-flop 24 and to a programming transmitter 27. Normally open switch 29 is connected between flip-flop 24 and a source of positive potential B+ such that closure of the switch 29 will clock the Q terminal of flip-flop 24 high. Thereafter, an output from pulse shaper 22 resulting from the detection of a stimulation signal by pick-up antenna 20 will result in two high inputs to AND gate 25 and activation of delay circuit 26. Delay circuit 26 may be of any type known to the prior art which will provide an output signal a predetermined time after it receives an input signal. Delay circuit 26 is activated by the first stimulation signal appearing on lead 16 that is detected by pick-up antenna 20 following the closing of switch 29. That is, closing of switch 29 causes the Q output of flip-flop 24 to go high resulting in one high input to AND gate 25. Detection of a stimulation signal on lead 16 results in a high output from pulse shaper 22 and a second high input to AND gate 25, the resulting high output from AND gate 25 activating delay circuit 26. Preferably, the delay of delay circuit 26 is sufficient to delay its output until the stimulation signal that resulted in its activation is terminated. Most preferably, the delay is sufficient to delay the output of delay circuit 26 for a predetermined period of time following a detected stimulation signal on lead 16. The predetermined period of time may be established such that the delay output is rendered during the refractory period of the tissue being stimulated by the electrode pair 17/18.

As noted above, the output of delay circuit 26 is connected to the reset terminal of flip-flop 24 to result in a resetting of flip-flop 24 after the delay of delay circuit 26. In addition, the output of delay circuit 26 is connected to a programming transmitter 27 to cause programming transmitter 27 to activate, after the delay period, to result in the transmission of radio frequency programming signal via transmitting antenna 28, in known manner. Programming transmitter 27 is of the type that may be set to establish one or more of the oprating characteristics of sense amplifier 11 and pulse generator 12 in cooperation with demodulator 13 and programming logic 14, and may employ any of the radio frequency techniques known to the prior art.

Obviously, many modifications and variations of the present invention are possible in light of the above teachings. For example, the teachings of the present invention are easily adaptable to a bipolar lead system.

One possible adaptation would be to have the sense amplifier 11 connected to a bipolar mode and keep the demodulator connected in a unipolar mode with one of the bipolar leads and indifferent electrode 18. Additionally, pick-up antenna 20 and transmitting antenna 28 need not be separate elements. Further, the detection of a stimulation signal need not be accomplished as described with reference to the Figure. Alternatively, the stimulation signal may be detected by a skin electrode which may then be processed in accordance with the teachings herein to result in a delay of the transmission of the programming signal. Of course, display 23, while described with reference to monitoring the programmed state of sense amplifier 11 and pulse generator 12, will also allow a determination that a desired programming has been accomplished by displaying the desired parameters following transmission of a programming signal. It is therefore to be understood that, within the scope of the appended claims, the invention may be practiced otherwise than as specifically described.

We claim:

1. In a body stimulation system of the type having external means for generating and transmitting radio frequency programming signals and implantable means, the implantable means including signal generator means with at least one programmable operating characteristic and means responsive to received programming signals for establishing said programmable operating characteristic in predetermined correspondence therewith; a housing enclosing said signal generator; and output means for delivering stimulation signals to a desired body site including stimulation delivering lead means extending from said housing, the improvement wherein said lead means comprises means connected to said operating characteristic establishing means for receiving said programming signals.

2. The body stimulation system of claim 1 wherein said external means comprises means for preventing the transmission of programming signals during a stimulation signal.

3. The body stimulation system of claim 2 wherein said transmission preventing means comprises means for preventing transmission of programming signals for a predetermined period following a stimulation signal.

4. The body stimulation system of claim 1 comprising means for activating said external means during the refractory period of the tissue at said desired body site.

5. The body stimulation system of claim 1 comprising means for rendering said output parameter establishing means responsive to received programming signals only during the occurrence of second externally generated signals having characteristics discriminable from the characteristics of said programming signals.

6. The body stimulation system of claim 5 wherein said programming signals comprise radio frequency signals and said second signal comprises magnetic signals.

7. The body stimulation system of claim 5 wherein said signal generator means comprises pulse generator means, said pulse generator means operating at a fixed rate during said second externally generated signals.

8. The body stimulation system of claim 7 wherein said external means comprises means for preventing the transmission of programming signals during a stimulation signal.

9. The body stimulation system of claim 8 wherein said transmission preventing means comprising means for preventing transmission of programming signals for a predetermined period following a stimulation signal.

10. The body stimulation system of claim 9 wherein said programming signals comprise radio frequency signals and said second signal comprises magnetic signals.

11. The body stimulation system of claim 7 comprising means for activating said external means during the refractory period of the tissue at said desired body site.

* * * * *

UNITED STATES PATENT AND TRADEMARK OFFICE
CERTIFICATE OF CORRECTION

PATENT NO. : 4,440,173

DATED : April 3, 1984

INVENTOR(S) : Lawrence C. Hudziak et al.

It is certified that error appears in the above-identified patent and that said Letters Patent are hereby corrected as shown below:

Column 2, line 58, the word appearing as "and" should read --an--.

Column 4, line 57, after the word "of" and before the word "radio", insert --a--.

Column 5, line 2, the word appearing as "to" should read --in--.

Signed and Sealed this

Eleventh Day of September 1984

[SEAL]

Attest:

Attesting Officer

GERALD J. MOSSINGHOFF

Commissioner of Patents and Trademarks